United States Patent [19]

Bercik et al.

[11] 4,153,638

[45] May 8, 1979

[54] OLEFIN POLYMERIZATION PROCESS

[75] Inventors: Paul G. Bercik, Trafford; Harold E. Swift, Gibsonia; Kirk J. Metzger, Pittsburgh, all of Pa.

[73] Assignee: Gulf Research & Development Company, Pittsburgh, Pa.

[21] Appl. No.: 876,757

[22] Filed: Feb. 10, 1978

Related U.S. Application Data

[63] Continuation-in-part of Ser. No. 454,403, Mar. 25, 1974, abandoned, which is a continuation-in-part of Ser. No. 362,925, May 22, 1973, abandoned.

[51] Int. Cl.$^2$ ............................................. C07C 3/10
[52] U.S. Cl. .................................. 585/526; 252/458; 252/459; 585/533; 585/666
[58] Field of Search ............................ 260/683.15 R

[56] References Cited

U.S. PATENT DOCUMENTS

| | | | |
|---|---|---|---|
| 2,658,875 | 11/1953 | Schuit et al. | 252/459 |
| 3,173,855 | 3/1965 | Miale et al. | 260/683.65 |
| 3,236,762 | 2/1966 | Rabo et al. | 260/683.15 |
| 3,252,757 | 5/1966 | Granquist | 208/120 |
| 3,325,465 | 6/1967 | Jones et al. | 260/683.15 |
| 3,402,217 | 9/1968 | Engelbrecht et al. | 260/683.15 |
| 3,534,114 | 10/1970 | Bushick | 260/683.65 |
| 3,644,565 | 2/1972 | Biale | 260/683.15 |
| 3,655,798 | 4/1972 | Csicsery et al. | 260/683.65 |
| 3,729,429 | 4/1973 | Robson | 252/458 |

*Primary Examiner*—C. Davis

[57] ABSTRACT

$C_2$–$C_5$ mono-olefins are polymerized in the presence of a metal-substituted synthetic mica montmorillonite catalyst to selectively form gasoline boiling range oligomer products containing from 5 to 12 carbon atoms and oligomer distillate products containing up to 24 carbon atoms and having a maximum distillation end point of about 750° F. (399° C.).

12 Claims, No Drawings

OLEFIN POLYMERIZATION PROCESS

CROSS REFERENCE TO RELATED APPLICATION

This application is a continuation-in-part of application Ser. No. 454,403, filed Mar. 25, 1974, which is a continuation-in-part of application Ser. No. 362,925, filed May 22, 1973, both of which are now abandoned. The disclosure of the parent applications, particularly so much of the specifications relating to catalyst preparation and the employment of the prepared catalyst in the mono-olefin polymerization process, is incorporated herein by reference thereto.

BACKGROUND OF THE INVENTION $C_2$–$C_5$ olefins are produced in various thermal and catalytic petroleum refining operations. To some extent these olefins can be employed in the production of petrochemicals. However, substantial quantities of these olefins must be utilized in the production of gasoline and/or distillate products.

The alkylation of isobutane with $C_3$ and $C_4$ olefins, for example, is widely practiced to produce high octane, low sensitivity gasoline. To a lesser extent polymerization processes are used to convert $C_2$–$C_5$ olefins to higher boiling, more valuable hydrocarbon fractions. In some instances, various combinations of alkylation and polymerization are used to convert light olefins to gasoline and heavier hydrocarbons. The combination of alkylation and polymerization is particularly useful in those situations where isobutane is in short supply.

In the sulfuric acid alkylation of isobutane it is conventional to employ a $C_4$ hydrocarbon mixture as a feed to the process. Refinery $C_4$ hydrocarbon mixtures normally are comprised of isobutane, isobutylene, butene-1, butene-2 and normal butane. Isobutylene tends to produce inferior alkylation products, has the lowest yields, and has the highest acid consumption of any of the olefins present in the feed. Under such circumstances, it may be desirable to separate the isobutylene fraction from the feed by, for example, selectively dimerizing the isobutylene to produce a dimer having a high clear research octane number and high clear research and motor octane blending values.

In the hydrofluoric acid alkylation of isobutane, butene-1 and pentene-1 alkylate much less favorably with isobutane than the corresponding internal olefins. Therefore, it would appear to be desirable to isomerize the butene-1 and pentene-1 fractions prior to employing the olefins in the alkylation process. It is readily apparent that a single process which would selectively dimerize isobutylene while simultaneously isomerizing butene-1 to butene-2 and pentene-1 to pentene-2 would be highly desirable in preparing the feed to the alkylation process.

In Europe, the alkylation of light olefins is practiced to a limited extent because of the relatively moderate market for gasoline. However, propylene dimerization processes to make methyl pentenes are of interest to provide a high clear research octane front end gasoline blending component. Polymerization of $C_3$–$C_4$ olefins to low pour oligomer distillates should become widespread as more and more propylene and butylene by-products become available from new ethylene plants.

Isobutylene and other olefins, particularly mono-1-olefins, have been polymerized utilizing a catalyst comprising a crystalline aluminosilicate in hydrogen form. It is also known that catalyst compositions such as the Y-zeolites can be employed for dimerizing isobutylene for short process periods. However, the useful lives of the prior art catalysts are limited by the formation of heavy polymer that is incapable of being diffused out of the active cage-like cavities wherein dimerization and subsequent trimerization, etc. occurs. Such catalysts after short polymerization periods contain large concentrations of heavier polymer, as measured by carbon value determinations made on the catalyst, and so become substantially inactive.

SUMMARY OF THE INVENTION

By the invention, $C_2$–$C_5$ mono-olefins are polymerized in the presence of a metal-substituted synthetic semi-crystalline aluminosilicate catalyst to selectively form gasoline boiling range and heavier hydrocarbon fractions.

DESCRIPTION OF THE INVENTION

The invention is applicable to the polymerization of $C_2$–$C_5$ mono-olefins to form oligomer products containing a limited number of monomer units. As employed in this invention, the term oligomer will be used to define polymer products containing from 5–24 carbon atoms per molecule. The $C_2$–$C_5$ mono-olefins employed in the process of this invention may be straight chain or branched chain.

The process is particularly applicable in polymerizing $C_2$–$C_5$ mono-olefin streams produced in petroleum catalytic cracking processes wherein the products contain minimal concentrations of diolefins. The concentration of diolefins in the feed to the hereafter described polymerization process is preferably maintained at less than 1 weight percent. Mono-olefin streams containing more than one percent diolefins can be subjected to selective diolefin hydrogenation or solvent extraction to reduce the diolefin content prior to processing by this invention.

The catalyst employed in the process of this invention is selected from the group of nickel or cobalt substituted semi-crystalline aluminosilicates which are synthetic and which are predominately ordered in two directions, that is, which are laminar or have a layered or stacked sheet structure, and are highly active. The catalysts employed in the process of this invention are described in U.S. Letters Patent No. 3,966,642, issued June 29, 1976. Reference is made to the aforementioned patent for a complete description of the catalyst composition and its method of preparation. So much of the patent is incorporated herein by reference thereto. The catalyst employed in the polymerization process of this invention comprises:

a laminar 2:1 layer-lattice aluminosilicate mineral possessing layer-lattice unit cells, each cell having an inherent negative charge balanced by cations exterior to said unit cell, said mineral corresponding to the following overall formula prior to drying and calcining:

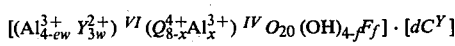

Where Y is selected from the class consisting of nickel, cobalt and mixtures thereof;

Q is at least 0.95 mol fraction silicon ions, the remainder consisting of tetravalent ions having an ionic radius not to exceed 0.65 Å;

C is at least one charge-balancing cation; and where e has a numerical value from 2 to 3 inclusive;

w has a numerical value from 0.01 to 2 inclusive, with the proviso that the quantity ew have a numerical value from 0.02 to 4 inclusive;

f has a value of 4 or less;

x has a numerical value from 0.05 to 2.0 inclusive;

y is the valence of the cation C;

d is the number of cations C where the product $dy = x + 3(e-2)w$;

In the above formulation, the first bracket represents the overall average laminar layer-lattice unit cell structure formulation, which, as will be explained hereinbelow, possesses an inherent negative charge by reason of the fact that the positive charges of the cations are less than the negative charges of the anions. Since the preparation as a whole is electrostatically neutral, the charge-balancing cations which are necessarily present are external to the lattice and are represented by the second bracket, in which C stands for the charge-balancing cations taken as a whole, with y being their average charge and d being the number of charge-balancing cations per unit cell. It will be recognized that in this formulation, C may actually correspond to a large variety of charge-balancing cations simultaneously present, such as, for example, a mixture of hydrogen, calcium, and the like cations. For catalytic purposes, it is preferred that the mineral be free or contain only low concentrations of alkali metals which can occur in the exchange sites (C) due to the presence of alkali metals, for example, in the preparative solutions. Minor amounts of alkali metals, such as 5 percent to 10 percent of the exchange sites, or as much as 35 percent of the exchange sites, can be tolerated.

In the above statement of the nature of Q, it will be noted that those substituents other than silicon are designated in terms of ionic radius and ionic charge. It is further clear from the formulation given that Y consists of nickel or cobalt ions either isomorphously substituted for a like number of aluminum ions, whereby a charge deficit results, or substituted on the basis of three divalent ions for two aluminum trivalent ions with no resulting charge deficit, or a mixture of both. In like manner, it is clear that Q, while consisting predominantly of silicon ions, may include a minor proportion of tetravalent ions isomorphously substituted for some of the silicon ions without affecting the overall charge while trivalent aluminum ions in a proportion represented by subscript x are isomorphously substituted for a like number of silicon ions, whereby a charge deficit results from the substitution of a trivalent ion for a tetravalent ion.

The specific elements which are included in the above formulation other than aluminum and silicon are relatively small in number, because of the limitations imposed by the stipulated ionic charge and ionic radius.

For the sake of convenience, a tabulation follows in which the Y and Q elements usable in accordance with the invention are listed. It will be clear that this listing results from checking each element against its known valence states and its known ionic radius for each applicable valence state, taking into account the coordination number where the latter affects the ionic radius. Tables of ionic radii for various elements have appeared in the literature during the last half century, and in the case of disparity among the values given for a specified element, the best value has been chosen in the light of all of the known data, and this best value is the one which appears in the tables which follows:

| TABLE A | | |
|---|---|---|
| Y: | Divalent - Maximum 0.75 A | |
| Nickel | (Ni) | 0.69 |
| Cobalt | (Co) | 0.72 |

| TABLE B | | |
|---|---|---|
| Q: | Tetravalent - Maximum 0.65 A | |
| Silicon | (Si) | 0.41 |
| Germanium | (Ge) | 0.53 |

Preferably, in the above unit cell formula, Y is nickel, cobalt or mixtures thereof; and Q is silicon. Further, the value of e is preferably about 2; the value of w from 0.2 to 1.66 with the value of ew being preferably from 0.4 to 3.32. The value of x is preferably from 0.5 to 2, and the value of f is preferably from 0.5 to 3.75.

Moreover, usually, although not necessarily, the composition of the charge-balancing cations in the second bracket contains some proportion of the partial hydroxides of aluminum. In accordance with a more particular formulation, the composition of the charge-balancing cations in the second bracket contains some proportion of the partial hydroxides of aluminum. Thus, in accordance with a more particular formulation, the composition of the charge-balancing cations in the second bracket may conveniently be represented as follows:

$$[a\ M^n + b\ Al\ (OH)_{3-z}]$$

wherein $$an + bz = dy = x + 3(e-2)w$$

and M is at least one charge-balancing cation and is preferably selected from the group consisting of hydrogen; ammonium; substituted ammonium; substituted phosphonium; multivalent metal cations other than aluminum; and partial hydroxides of multivalent metal cations; and n is the unsatisfied valence of M. In practice, the product bz is a small value compared to the product an.

This second, more particular characterization of the charge-balancing cations is believed to correspond more closely to the products initially obtained in accordance with the preferred mode of preparation. Moreover, it provides explicitly for any hydroxyaluminum cations which may be present. It will be understood that such hydroxyaluminum cations are commonly present as a mixture of species, as described, for example, in U. S. Geological Survey Water-Supply Paper 1827-A (1967), which is incorporated herein by reference. However, since these charge-balancing cations are essentially exchangeable without disturbing the lattice itself, the latter being represented by the first bracket, after having made a given preparation in accordance with the invention by a preferred procedure, it is relatively simple to exchange a portion of the cations represented by M or indeed substantially all of the cations represented by M in the second bracket for some other preselected cation or mixture of cations. The partial hydroxides of aluminum are exchangeable with difficulty, if at all. Thus, for example, referring to the first general formulation given hereinabove, the charge-balancing cation C can at will be selected from such diverse species as palladium, hydroxyaluminum, hydroxynickel, trimethylammonium, alkyl phosphonium, and the like cations and indeed mixtures thereof. Thus, C may be selected from the group consisting of alkaline earth metal, heavy metal, heavy metal partial hydroxides, ammonium, substituted ammonium, substituted phosphonium, and the like cations and mixtures thereof. As noted above, alkali metals are preferably excluded but may be present in minor amounts.

In the case of the use of substituted ammonium and substituted phosphonium ions and the like, the substituents should be such that they can be driven off during calcination of the mineral.

Those skilled in the art will recognize, accordingly, that the first bracket of the above formula relates to a fixed array of ions in a tripartite lamina which for convenience may be described as muscovite-like, and in which the positive ions shown in the first parentheses are in octahedral coordination with sheets comprising oxygen, hydroxyl, and fluoride ions; whereas the positive ions shown in the second parentheses in the first bracket are in tetrahedral coordination jointly with the aforesaid sheets of oxygen, hydroxyl, and fluoride ions, and also with sheets of oxygen ions in essentially a hexagonal ring array constituting the external faces of the tripartite lamina. The positive ions shown in the second bracket have no essentially fixed position, but are in effect external to the lattice of the tripartite lamina.

Those skilled in the art will also recognize that when some of the parameters in the above formulations have values outside of the stipulated ranges, the formulations reduce to representations of various end members of a broad group of laminar aluminosilicates, which of course are outside of the scope of the present invention. Thus, for example, when w and x both equal zero, and no fluoride ion is present, the first bracket describes the mineral pyrophyllite. It will also be seen that the factor d is equal to zero, when w and x equal zero, so that the ionic species set forth in the second bracket are not present, which of course results from the fact that the lattice of pyrophyllite is charge-balanced. Again, for the case in which x equals zero, w equals two, e equals two, and no fluoride is present, a mineral results in which the lattice is likewise charge-balanced, and the ionic species set forth in the second bracket are not present. Such a mineral is described in U.S. Pat. No. 2,658,875 to Cornelis et al.

In general, 2:1 layer-lattice aluminosilicate minerals, or in alternative nomenclature, tripartite aluminosilicate minerals of the type concerned in the present invention, may be classified as either dioctahedral or trioctahedral, depending upon whether the number of cations per unit cell in the octahedral (or inner) layer is approximately 4 or 6, respectively. The foregoing structural formula is, as stated, an overall formula for a given preparation, and the fact that the number of such octahedral cations may vary from 4 to 6 in a continuous manner in the formulation given does not means that a single lamina is present having such an intermediate number of cations. In point of fact, the individual laminae are believed to be either dioctahedral or trioctahedral, and in a given preparation the relative proportions of the dioctahedral and trioctahedral species will give rise to the numerical values obtained in quantitatively characterizing the preparation in accordance with the foregoing formula. Where e in the formulation is intermediate between 2 and 3, accordingly, both 1:1 and 3:2 substitutions are present. Because of the extremely small particle size of the minerals, the exact physical nature of these mixed phase systems is uncertain. In any case, in this specification, the term "a mineral" shall mean the 2:1 layer lattice products which are produced by simultaneously synthesizing both the dioctahedral and trioctahedral phases in place in a single reaction mixture. It may be emphasized that such mineral made for use in this invention is a single mineral species, even though it may contain two phases. The minerals of this invention, therefore, differ significantly from compositionally similar mixtures obtained by simply mixing together the separately synthesized dioctahedral and trioctahedral members.

The minerals in accordance with the invention are synthesized by a hydrothermal route. The procedure follows in a general way that is set forth in U.S. Pat. No. 3,252,757 to W. T. Granquist, except that the cited patent does not relate to the inventive aluminosilicates, which contain additional elements, so that the reaction mixtures required in the present invention are substantially different. As will be evident from the structural formula already given, the reaction mixture for the hydrothermal synthesis includes a source of one or more multivalent cations other than aluminum and silicon. For example, for the case of nickel, this may be a relatively soluble compound, such as, for example, nickel acetate, nickel fluoride, nickel nitrate, and the like; or it may be a relatively insoluble nickel compound such as nickel hydroxide. It is of interest that in general the inclusion of soluble nickel salts in the reaction mixture tends to cause the nickel to occur predominantly in the trioctahedral phase, while relatively insoluble nickel compounds promote its occurrence in the dioctahedral phase. The terms are well understood in the art, and a brief explanation in addition to that already given may be found on page 156 of the book by George Brown, "The X-Ray Identification and Crystal Structures of Clay Minerals", London 1961. The classical paper by Ross and Hendricks, "Minerals of the Montmorillonite Group", U. s. Geological Survey Professional Paper 205-B (1945) is helpful, particularly for its treatment of variation of the members of a given series of laminar aluminosilicate minerals.

For cobalt, the most commonly available simple inorganic and organic compounds thereof may in general be used, as will be evident to those skilled in the art.

The minerals after their preparation are activated for use as catalysts by drying and calcining. By drying is meant the removal of the external water of absorption by heating. Usually the drying temperatures are from 250° F. (121° C.) to 350° F. (177° C.) at atmospheric pressure, albeit higher and lower pressures can, of course, be employed. By calcining is meant the addition of heat to effect some chemical change in the catalyst such as the removal of chemically bound water or ammonia if the charge-balancing cation is $NH_4^+$. The calcining temperatures are normally from about 800° F. (427° C.) to about 1300° F. (704° C.). Atmospheric pressure is usually employed but higher or lower pressures can, of course, be used. The maximum calcination temperature should be below that temperature wherein a phase inversion may occur. Thus, dehydration of the dioctahedral phase may preferably occur at normal calcination temperatures but increased temperatures tend to result in dehydration of the trioctahedral phase which may then recrystallize to form a new undesired mineral species.

A preferred catalyst of this invention is prepared by calcining a nickel-containing mineral, i.e. $Y=Ni^{2+}$, with the preferred charge balancing ion being $H^+$ which is formed upon deamination of the $NH_4^+$ form of the mineral. As previously discussed, other charge balancing ions and combinations of charge balancing ions can be present, but $H^+$ is preferred with combinations of $Ni^{2+}$ and $H^+$ being next preferred, i.e. at site C of the unit cell formula. It should also be understood that the nickel-containing mineral or catalyst can be impregnated with various metal ions as will be subsequently described. If this is done, again the preferred ion to be impregnated is nickel. It should also be understood that during the synthesis of the mineral that minor amounts of other phases can form and co-exist with the finished dried mineral. The presence of such phases have little or no effect on catalyst activity. Such phases may consist mainly of gibbsite, $3NH_4F.AlF_3$, $NH_4F.AlF_3$ or combinations thereof when fluoride is the halogen used in the synthesis. The halogen-containing phases, if present, can be removed by extensive water washing; however, since they contribute little or nothing to catalytic activity, it is more economical to leave them in the finished catalyst. Thus, the fluoride (or any other halogen) content of the material synthesized can be higher than that required by the basic structural formula due to the presence of said above phases.

The minerals after drying and calcination are suitable in accordance with the invention as catalysts for the polymerization of $C_2-C_5$ olefins. In accordance with another aspect of this invention, the catalyst can comprise the minerals described above containing, in addition, a hydrogenation component deposited thereon. Any suitable hydrogenation component can be employed. For example, a suitable hydrogenation component would be one or more metals from Groups VI and/or VIII of the Periodic Table. These metals or combinations of metals are deposited on the minerals described above and do not form a part of the mineral structure. The preferred hydrogenating components are nickel and cobalt and in particular nickel.

The amount of the hydrogenation component will depend somewhat on the metal or combination of metals chosen. The platinum group metals are usually used in a concentration of 0.01 to 5 weight percent of the final catalyst, usually from 0.10 to 1.0 weight percent. The other metals from Groups VI and VIII are normally used in higher concentrations on the other of 0.2 to 20 weight percent.

The method of deposition of the hydrogenation component is not critical and any method well known in the art can be employed, such as, for example, the deposition of the hydrogenation component onto a dried or heat activated mineral from a solution of the aqueous salts of the metals. The technique of minimum excess solution can suitably be employed, or an aqueous solution of the desired metal, such as nickel nitrate, can be added to an aqueous slurry of the formed mineral without intermediate drying or calcining. The hydrogenation component can also be added using techniques known in the art for exchanging metal ions with solid inorganic exchanges, such as zeolites. Also, the hydrogenation component can be added as a result of the reaction of a metal salt with the base material especially when $[dC^y]$ is $H^+$ or $NH_4^+$. For example, if $NiCl_2$ is intimately mixed in the dry state with the hydrogen form of the structure on page 2, and then heated, HCl can be evolved with the result that Ni is dispersed uniformly throughout the structure.

After the deposition of the hydrogenation component, the composition is suitably activated by drying under the usual conditions following by calcining, again under the usual conditions.

The catalyst employed in the polymerization process can be in the oxide, reduced or sulfided form. With the catalyst in the oxide or reduced form the olefin feed of the polymerization process should contain less than 3, and preferably less than 1 parts per million (ppm) sulfur. When the sulfided form of the catalyst is employed, the sulfur content of the olefin feed can be in the range of 0 to 3,500 ppm and preferably 0 to 80 ppm. In selective polymerization reactions as hereafter described, the olefin feed should contain at least 5 ppm sulfur to ensure proper selectivity. Generally, in the employment of the sulfided catalyst the sulfur depresses activity and increases selectivity in the preparation of gasoline boiling range oligomers. Although in properly sulfided catalysts there are no significant aging or catalyst composition changes noted with minor sulfur concentrations in the olefin feed, employing the reduced or oxide forms of the catalyst will result in sulfiding the metal form of the catalyst with subsequent permanent loss in activity with significant concentrations of sulfur in the feed. The sulfur concentration of the olefin feed to the polymerization process which is in the form of mercaptans or hydrogen sulfide can be reduced or substantially eliminated by conventional processes such as a caustic washing step.

In obtaining the sulfided form of the catalyst, conventional presulfiding procedures can be employed. For example, the calcined catalyst can be presulfided by passing a gaseous hydrogen and hydrogen sulfide mixture at a pressure in the range of 500–800 psig and a temperature in the range of 600° F.–750° F. (315.6°–398.9° C.) until an exposure of 1 gram of sulfur per gram of nickel and/or cobalt in the catalyst is obtained. Preferably, when employing the sulfided form of the catalyst in selective polymerization reactions, a two-step presulfiding process is employed.

A suitable feed to the polymerization process of this invention is derived from absorber gases obtained from catalytic cracking operations. The acid gases present in these absorber gases can be removed prior to the polymerization process by conventional amine scrubbing of the gases. Generally, the combined carbon monoxide and carbon dioxide concentrations of the mono-olefin feed to the polymerization process should be less than 0.4 mol percent and preferably less than 0.1 mol percent.

In addition to controlling the concentration of sulfur and acid gases in the olefin feed, it is desirable for extended catalyst life to limit the concentration of basic nitrogen in the olefin feed to a maximum of 2 ppm and preferably less than 0.3 ppm. A conventional water washing step, preferably under mildly acidic conditions is effective for separating basic nitrogen compounds from the olefin feed. This water washing step can follow the caustic washing and/or amine scrubbing steps previously described.

The mono-olefin feed to the polymerization process can contain an equilibrium concentration of water, normally in the range of 50 to about 120 ppm. Preferably, the olefin feed should be dried over a suitable adsorbent such as 3A molecular sieves or activated bauxite to obtain a product containing less than 10 ppm dissolved water.

The sulfided form of the catalyst is particularly effective in the polymerization of $C_2$–$C_4$ mono-olefins to obtain low pour distillate oligomers boiling generally in the range of 200°–800° F. (93°–427° C.). Absorber gas, as previously described, typically contains essentially equal molar quantities of ethylene and propylene and so can be advantageously processed to obtain the distillate oligomers. Propane-propylene, butane-butylene streams, or mixtures thereof, can also be employed as feeds to the polymerization zone employing process conditions hereafter described to obtain the aforementioned low pour oligomer products. Polymerization conditions generally comprise 250°–480° F. (121°–249° C.), 0.5 to 4.0 liquid weight hourly space velocity, and 400–1500 psig (28.2–105.8 kilograms/square centimeter). Conversions per pass of 40 to 90 percent under the stated process conditions can be obtained. Unconverted monomer and paraffin recovered from the product can be recycled so as to increase overall conversion and so as to quench and control reaction temperature. Additionally, if heavier oligomer product was desired, the dimer separated from the polymerization product can be recycled to increase the yield of trimer and heavier distillate. The novel distillate product processes can be operated to produce an oligomer product having more than 75 percent by weight of the oligomer boiling above 200° F. (93° C.).

The oligomer distillate products of the invention can be hydrogenated to obtain high performance jet fuels as characterized by low freeze points, high gravimetric heat contents, high lumenometer numbers, high smoke points, and outstanding thermal stability, or low pour point lubricating oils or hydraulic fluids.

The sulfided form of the catalyst is particularly effective in the selective polymerization of the tertiary alpha olefins to include isobutylene and 2 methyl-butene-1 to form high octane gasoline boiling range dimers, codimers, trimers, cotrimers and mixtures thereof. Under the same process conditions, the simultaneous isomerization of butene-1 to butene-2 and pentene-1 to pentene-2 and 3 methyl-butene-1 to 2 methyl-butene-2 can be achieved. In addition, the simultaneous polymerization of minor concentrations of diolefins present as impurities, and in particular butadiene, to $C_{16}$ plus product can be achieved.

In the production of gasoline boiling range oligomer products from tertiary alpha olefins process conditions generally comprise a temperature in the range of 120° to 380° F. (49° to 193° C.), a liquid weight hourly space velocity in the range of 0.5 to 4.0, and a pressure in the range of 400 to 1500 psig (28.2 to 105.8 kgs/cm$^2$).

In the selective polymerization of tertiary alpha olefins to produce gasoline boiling range oligomers, a particularly suitable feed is the $C_4$ hydrocarbon mixture obtained as a product of catalytic cracking processes. Such $C_4$ mixtures contain less than 10 percent and typically less than 5 percent by weight of $C_3$ or $C_5$ hydrocarbons and less than 0.5 percent by weight butadiene. Gasoline boiling range oligomers can also be produced from propane-propylene and butane-butylene streams. With such $C_3$–$C_4$ feed mixtures, butylenes would normally comprise about 40 to 60 liquid volume percent of the feed olefins. A $C_3$–$C_4$ feed would generally contain less than 7 and typically less than 3 percent by weight $C_5$ hydrocarbons and less than 3 percent, typically less than 1 percent, by weight $C_2$ hydrocarbons.

The selective tertiary alpha olefin process for the production of gasoline boiling range oligomers can also be applied to mixed propane-propylene, butane-butylene, and pentane-pentene streams. The feed olefins can comprise by liquid volume 30 to 50 percent propylene, 30 to 50 percent butylene, and 10 to 30 percent pentenes.

Isobutylene oligomerization to form gasoline boiling range products on a weight basis will range from 50 to 95 percent, normally at least 65 percent, 50 to 85 percent, and 50 to 80 percent, respectively with the above described $C_4$, $C_3$–$C_4$, and $C_3$–$C_5$ streams. The extent of 2-methyl butene-1 oligomerization will range from 50–80 percent with the above mentioned $C_3$–$C_5$ stream. Oligomerization of terminal mono-olefins, excluding the tertiary terminal mon-olefins, will be less than 15 percent, normally less than 5 percent by weight of their concentration in the feed.

The $C_3$–$C_5$ mono-olefins remaining in the polymerization product are further enriched in internal olefins by means of double bond isomerization; the n-butene product will normally contain on a weight basis, 80 to 95 percent butene-2 and the $C_5$ mono-olefins will consist of 70 to 95 percent internal olefins. Normally, at least 75%, on a weight basis, of the butene-1 is isomerized to butene-2. The liquid oligomer product generally contains less than 10 percent by weight of a fraction boiling higher than 415° F. (213° C.). Under the specified conditions, the liquid oligomer product will have clear research octane numbers of 100.5 to 103, 99 to 101, and 98 to 100 when prepared from the above-described $C_4$, $C_3$–$C_4$, and $C_3$–$C_5$ streams, respectively.

With the mixed propylene-butylene feed described above, the amount of $C_3$–$C_4$ olefins that are oligomerized or co-oligomerized to gasoline boiling range oligomers may be increased by increasing the severity of the operation. Here, conversion to predominantly gasoline boiling range oligomers is 85 to 98 percent for isobutylene and 12 to 40 percent for propylene and butene-1. The liquid oligomer product has a Clear Research Octane Number of 98–100 and comprises less than 12 percent by weight material boiling outside the gasoline range taken as 415° F. plus.

The co-oligomerization of $C_3$–$C_4$ olefins can be controlled by introducing a portion of the olefin feed into a lower or downstream region of the polymerization reactor with the major portion of the olefin feed being introduced into the top or upstream portion of the polymerization zone. By introducing a portion of the olefin feed into a downstream region of the polymerization zone in the middle 1/3 portion of the reaction zone, for example, the degree of co-oligomerization can be controlled. Co-oligomerization can further be enhanced by segregating a portion of the butane and butenes in the $C_3$–$C_4$ olefin feed and introducing this segregated portion of the feed into an intermediate region of the polymerization zone.

The oxide form, or optionally the reduced form, of the catalyst composition can be employed to convert linear $C_2$–$C_4$ alpha olefins to oligomers boiling predominantly in the gasoline range, co-oligomers, or mixtures thereof. Care must be taken in the practice of this aspect of the invention to maintain a sulfur concentration below 1 part per million in the olefin feed so as to maintain the catalyst in the oxide or reduced form during the polymerization process. Mild process conditions comprising a temperature in the range of 80° to 300° F. (27° C. to 149° C.), a pressure in the range of 400 to 1,500 psig (28.2 to 105.8 kgs./cm.$^2$), and a liquid weight hourly space velocity in the range of 1.0 to 8.0 can be employed. The conversion per pass of the olefin feed can range from 35 to 95 percent.

A useful application of this aspect of the invention involves co-dimerization of the ethylene and propylene to pentenes. A conventional source of this type of feed material is an absorber gas from a catalytic cracker. The liquid product of the polymerization process can contain at least 25 percent pentenes.

Another useful application of the oxide or reduced form of the catalyst comprises dimerizing propylene to methyl pentene. Under such conditions, the liquid oligomer product would contain at least 25 percent by weight methyl pentene. With a $C_2$–$C_3$ or $C_3$ olefin feed the liquid oligomer product will have a clear research octane in the range of 94.5 to 98.0 and would contain no less than 80 percent by weight of a gasoline boiling range fraction.

The oxide or reduced form of the catalyst can also be used to polymerize $C_2$–$C_4$ olefins to form oligomer distillate products.

The oxide or reduced form of the catalyst can also be used to selectively dimerize tertiary alpha olefins employing process parameters previously described. However, these forms of the catalyst must be subject to a substantial initial break-in activity period before a selective stable operation is achieved. Furthermore, the degree of simultaneous double bond isomerization achieved would be lower than that achieved employing the sulfide form of the catalyst. Under such conditions the normal butene product of the polymerization process may contain as low as 70 percent butene-2. Again, as previously noted with respect to the oxide and reduced forms of the catalyst, the sulfur content of the feed must be maintained below 1 part per million so as to maintain the catalyst in the oxide or reduced form.

The following examples are presented to illustrate objects and advantages of the invention. It is not intended to limit the invention to embodiments presented therein.

EXAMPLE 1

In this example two polymerization runs were made employing the novel polymerization catalyst to produce an oligomer distillate product from a mixed $C_3$–$C_4$ hydrocarbon feed containing propylene. The catalyst employed in these polymerization runs was the hydrogen form of the synthetic mica montmorillonite containing 13.8 weight percent nickel (substantially all of the nickle in the substituted form) and 3.6 weight percent fluorine. In synthesizing the catalyst, nickel was added by means of nickel fluoride. The hydrogen form was obtained via oven calcination in air at 1000° F. (538° C.) overnight prior to charging to the reactor. The catalyst was in the form of 1/16 inch extrudates. The catalyst had been calcined at a temperature of 927° F. (497° C.), a pressure of 25 psig (1.8 kgs./cm.$^2$), and at a space velocity of 805 standard gas volumes of dry air per hour per volume of catalyst for two hours. The calcined catalyst was thereafter presulfided at a temperature of 649° F. (343° C.), a pressure of 600 psig (42.3 kgs./cm.$^2$), and at a space velocity of 287 standard gas volumes of 98.5 volume percent hydrogen and 1.5 volume percent hydrogen sulfide per hour per volume of catalyst for 23 hours until an exposure of 1.0 grams of sulfur per gram of nickel in the catalyst was obtained. In a second sulfiding step, the catalyst was treated with isobutane containing 1.8 weight percent methyl mercaptan for 10 hours at 140° F. (60° C.), a pressure of 600 psig (42.3 kgs./cm.$^2$), and at a space velocity of 0.92 liquid weight per hour until 0.63 gram of sulfur had been exposed to each gram of nickel in the catalyst composition.

The feed to the polymerization process had the following composition:

TABLE I

|  | Weight Percent |
|---|---|
| Ethylene | 0.0 |
| Ethane | 0.1 |
| Propylene | 39.3 |
| Propane | 12.1 |
| Isobutane | 24.3 |
| Butene-1 | 0.0 |
| Isobutylene | 0.0 |
| N-Butane | 24.0 |
| Trans-2-Butene | 0.0 |
| Cis-2-Butene | 0.1 |

The feed was dried over 3 Angstrom molecular sieves to less than 5 ppm water prior to charging to the polymerization reactor. The feed was free of trace amounts of combined nitrogen and sulfur.

The polymerization process conditions employed with the above defined catalyst and feed compositions for each of the runs are shown below in Table II.

TABLE II

|  | Run No. 1 | Run No. 2 |
|---|---|---|
| Average Temp., °F. | 314 (157° C.) | 325 (163° C.) |
| Pressure, psig | 900 (63.3 kg/cm$^2$) | 900 (63.3 kg/cm$^2$) |
| Space velocity (liquid wt. hourly) | 0.96 | 0.98 |
| Catalyst, grams | 268.5 | 268.5 |
| Catalyst age, days | 8.7 | 9.7 |

Analyses of the products obtained in the polymerization Runs 1 and 2 indicates that 78.4 percent of the propylene was converted in Run No. 1 and 79.5 percent of the propylene was converted in Run No. 2. The complete analyses of the products obtained in the runs are shown below in Table III.

TABLE III

|  | Run 1, Wt. % | Run 2, Wt. % |
|---|---|---|
| $C_1$—$C_2$ | 0.1 | 0.2 |
| Propane | 12.4 | 12.7 |
| Butanes | 51.6 | 52.6 |
| Pentanes | 0.0 | 0.0 |
| Propylene | 8.5 | 8.1 |
| Butenes | 0.1 | 0.1 |
| Pentenes | 0.0 | 0.1 |
| Polymer, $C_6+$ | 27.2 | 26.2 |

The oligomer product obtained in each of the runs was analyzed to determine distribution of the oligomer fractions with the results shown below in Table IV.

TABLE IV

|  | Run 1, Wt. % | Run 2, Wt. % |
|---|---|---|
| Dimer | 2.3 | 2.6 |
| Trimer | 27.9 | 28.3 |
| Tetramer | 28.1 | 27.2 |
| Pentamer and Hexamer | 28.8 | 28.4 |
| Heptamer and Heavier | 13.0 | 13.6 |

The oligomer products of the runs were distilled employing the procedure outlined in ASTM D86 with the results shown below in Table V.

Table V

|  | Run 1 | Run 2 |
|---|---|---|
| OP, °F. | 111° F. (44° C.) | 117° F. (47° C.) |
| EP, °F. | Terminated at 90.5% Condensed | Terminated at 88% Condensed |
| Percent Condensed at 760 mm |  |  |
| 5 | 222° F. (106° C.) | 214° F. (101° C.) |
| 10 | 260° F. (127° C.) | 256° F. (124° C.) |
| 20 | 292° F. (145° C.) | 290° F. (143° C.) |
| 30 | 314° F. (157° C.) | 315° F. (157° C.) |
| 40 | 340° F. (171° C.) | 346° F. (174° C.) |
| 50 | 371° F. (189° C.) | 379° F. (193° C.) |
| 60 | 402° F. (206° C.) | 416° F. (213° C.) |
| 70 | 442° F. (228° C.) | 458° F. (237° C.) |
| 80 | 491° F. (255° C.) | 512° F. (277° C.) |

Some of the oligomer products from these two runs were composited and then fractionated in a precision distillation column to obtain specific oligomer concentrates. The analyses obtained on these oligomer concentrates are shown below in Table VI.

TABLE VI

| Oligomer Cut | Dimer | Trimer | Tetramer | Pentamer and Hexamer | Heptamer and Heavier |
|---|---|---|---|---|---|
| Inspections |  |  |  |  |  |
| Gravity, °API | 81.4 | 59.8 | 51.5 | 44.8 | 35.1 |
| Clear Research Octane No. | 97.8 | 98.7 | 98.7 | — | — |
| Clear Motor Octane No. | — | 82.0 | 82.1 | — | — |
| Freeze Point ASTM D2386: °F. | — | — | −112(−80° C.) | −92(−69° C.) | — |
| Pour Point, ASTM D97: °F. | — | — | — | — | −56(−49° C.) |
| Distillation, ASTM D86 |  |  |  |  |  |
| OP, °F. | — | 236(113° C.) | 324(162° C.) | 422(234° C.) | — |
| EP, °F. | — | 302(150° C.) | 409(210° C.) | 504(263° C.) | — |
| Percent Condensed at 760 mm Hg: °F. |  |  |  |  |  |
| 5 | — | 248(120° C.) | 340(171° C.) | 433(233° C.) | — |
| 10 | — | 250(121° C.) | 342(172° C.) | 436(225° C.) | — |
| 20 | — | 254(123° C.) | 346(175° C.) | 439(227° C.) | — |
| 30 | — | 258(126° C.) | 349(176° C.) | 442(229° C.) | — |
| 40 | — | 261(128° C.) | 351(177° C.) | 446(231° C.) | — |
| 50 | — | 265(130° C.) | 354(178° C.) | 450(232° C.) | — |
| 60 | — | 268(131° C.) | 356(180° C.) | 455(235° C.) | — |
| 70 | — | 271(133° C.) | 359(181° C.) | 460(238° C.) | — |
| 80 | — | 275(135° C.) | 365(184° C.) | 468(242° C.) | — |
| 90 | — | 282(139° C.) | 372(189° C.) | 478(248° C.) | — |
| 95 | — | 289(144° C.) | 377(192° C.) | 486(253° C.) | — |

These data show that all the oligomer fractions in the kerosine boiling range (tetramer thru hexamer) have very low freeze points and could therefore be useful in preparing isoparaffinic high performance jet fuels by means of hydrogenation. Likewise, the oligomer fractions in the lubricating boiling range, heptamer and heavier, has a very low pour point and could be useful in preparing isoparaffinic low pour hydraulic and transformer oils by means of hydrogenation.

EXAMPLE 2

In this example an isothermal polymerization run was made employing the novel polymerization catalyst to selectively dimerize isobutylene while simultaneously isomerizing butene-1 to butene-2 contained in a $C_4$ hydrocarbon feed mixture. The catalyst employed in the polymerization run was the hydrogen form of the synthetic mica montmorillonite containing 14.0 weight percent nickel (substantially all of the nickle being in the substituted form) and 4.0 weight percent fluorine. The hydrogen form was obtained via oven calcination in air at 1000° F. (538° C.) overnight prior to charging the reactor. The catalyst was in the form of 1/16 inch extrudates and had been prepared by the nickel acetate preparation procedure described in application Ser. No. 291,263. The catalyst had been calcined at a temperature of 930° F. (499° C.), a pressure of 25 psig (1.8 kgs/cm²) and at a space velocity of 480 standard gas volumes of dry air/hour/volume of catalyst for 2 hours. The calcined catalyst was thereafter presulfided at a temperature of 659° F. (348° C.), a pressure of 600 psig (42.2 kgs/cm²), and at a space velocity of 278 standard gas volume of 98.5 volume percent hydrogen and 1.5 volume percent hydrogen sulfide per hour per volume of catalyst for 24 hours until an exposure of 1.62 grams of sulfur per gram of nickel in the catalyst was obtained.

In a second sulfiding step, the catalyst was treated with isobutane containing 1.14 weight percent sulfur as methyl mercaptan for 12 hours at 142° F. (61° C.), a pressure of 600 psig (42.2 kgs/cm²) and at a space velocity of 1.03 liquid weight hourly until each gram of nickel in the catalyst composition had been exposed to 1.01 grams of sulfur. The prepared catalyst contained 0.79 atom of sulfur per atom of dispersed nickel.

The hydrocarbon feed to the polymerization zone was a butane-butene stream made in riser catalytic cracking and had the following compositions:

TABLE VII

|  | Weight Percent |
|---|---|
| Propylene | 1.5 |
| Propane | 1.6 |
| Isobutane | 33.6 |
| Butene-1 | 11.4 |
| Isobutylene | 11.1 |
| N-Butane | 10.4 |
| Trans-2-Butene | 14.9 |
| Cis-2-Butene | 10.4 |
| Isopentane | 3.4 |
| 2-Methyl-Butene-1 | 1.0 |
| N-Pentane | 0.1 |
| 2-Pentene | 0.2 |
| 2-Methyl-Butene-2 | 0.1 |
| Butadiene | 0.2 |

The butane-butene stream was water washed to lower the combined nitrogen content to 0.2 ppm and then dried over 3 Angstrom molecular sieves to less than 5 ppm water prior to introduction into the polymerization zone. The butane-butene stream contained 58 ppm sulfur after water washing.

The polymerization process conditions employed in the run with the above defined catalyst and feed compositions are shown below in Table VIII.

TABLE VIII

|  | Run 3 |
|---|---|
| Temp., °F. | 218(103° C.) |
| Pressure, psi | 600(42.3 kgs/cm$^2$) |
| Space Velocity (liquid wt. hourly) | 1.0 |
| Catalyst, grams | 190.2 |
| Catalyst age, days | 17.5 |

Analysis of the product obtained in polymerization Run 3 shows the following conversions of the olefins in the feed mixture and yield of C$_6$+ oligomer:

TABLE IX

|  | Conversion, Wt. Percent | Yield % Wt. C$_3$ — C$_4$ Olefins |
|---|---|---|
| Propylene | 12.1 | — |
| Butenes | 17.2 | — |
| Isobutylene | 70.9 | — |
| Butene-1 | 82.3 | — |
| Butene-2 | −35.9 | — |
| Total NC$_4$ | 0.9 | — |
| Butadiene | 91.8 | — |
| Total C$_3$ — C$_4$ Olefins | 17.4 | — |
| C$_6$ + Oligomer | — | 16.7 |

From the above it can be seen that only 0.9 percent of the normal butenes were polymerized and butene-2 formation was equal to 35.9 percent of the original amount. The butene-2 formation accounts for 96 percent of the total butene-1 conversion by means of isomerization. The butene-2 concentration in the normal butene product was 94.5 percent by weight and very closely approaches the equilibrium value of 95.6. Additionally, 70.9 percent of the isobutylene fraction was selectively polymerized to C$_6$+ gasoline boiling range oligomer product.

The oligomer product obtained in Run 3 was analyzed to determine distribution of the oligomer fractions with the results shown below in Table X.

TABLE X

|  | Weight Percent |
|---|---|
| Dimer | 63.8 |
| Trimer | 29.6 |
| Tetramer | 4.7 |
| Pentamer | 1.1 |
| Hexamer | 0.7 |

The oligomer product had an API gravity of 58.7 and a clear research octane number of 101.8.

The oligomer product was distilled employing the distillation procedure of Example 1 with the results shown below in Table XI.

TABLE XI

| OP, °F. | 140° F. (60° C.) |
|---|---|
| EP, °F. | 475° F. (246° C.) |
| Percent Condensed at 760 MM |  |
| 5 | 204° F. (96° C.) |
| 10 | 215° F. (102° C.) |
| 20 | 225° F. (107° C.) |
| 30 | 229° F. (109° C.) |
| 40 | 239° F. (115° C.) |
| 50 | 249° F. (121° C.) |
| 60 | 265° F. (129° C.) |

TABLE XI-continued

| 70 | 302° F. (150° C.) |
|---|---|
| 80 | 351° F. (177° C.) |
| 90 | 373° F. (189° C.) |
| 95 | 426° F. (219° C.) |
| Recovery % | 97.0 |
| Residue % | 2.0 |
| Loss % | 1.0 |

EXAMPLE 3

In this example, an adiabatic polymerization run (Run 4) was made employing the novel polymerization catalyst of Example 2 which was sulfided as in the process described in Example 2. The feed to the continuous polymerization process was a butane-butene stream made in catalytic riser cracker and had the following composition:

TABLE XII

|  | Weight Percent |
|---|---|
| Propylene | 1.5 |
| Propane | 1.6 |
| Isobutane | 32.3 |
| Butene-1 | 12.0 |
| Isobutylene | 11.7 |
| N-butane | 10.5 |
| Trans-2-Butene | 15.0 |
| Cis-2-Butene | 10.3 |
| Isopentane | 3.5 |
| 2-Methyl-Butene-1 | 1.0 |
| N-Pentane | 0.1 |
| 2-Pentene | 0.3 |
| 2-Methyl-Butene-2 | 0.0 |
| Butadiene | 0.2 |

The butane-butene stream was water washed to lower the combined nitrogen content to 0.3 ppm and then dried over 3 Angstrom molecular sieves to less than 5 ppm water prior to introduction to the polymerization zone. The butane-butene stream contained 68 ppm sulfur after water washing.

The polymerization process conditions employed in the run with the above defined catalyst and feed compositions are shown below:

TABLE XIII

|  | Run 4 |
|---|---|
| Temp., °F. |  |
| 1 | 208(98° C.) |
| 2 | 208(98° C.) |
| 3 | 208(98° C.) |
| 4 | 213(101° C.) |
| 5 | 226(108° C.) |
| 6 | 236(113° C.) |
| 7 | 243(117° C.) |
| Average | 221(105° C.) |
| Pressure, psi | 600(42.3 kgs/cm$^2$) |
| Space Velocity (Liquid wt. hourly) | 1.0 |
| Catalyst, grams | 155.2 |
| Catalyst age, days | 34.5 |

Analysis of the product obtained in polymerization Run 4 shows the following conversions of the olefins in the feed mixture and yield of C$_6$ plus oligomer:

TABLE XIV

|  | Conversion Weight Percent | Yield % C$_3$ — C$_4$ Olefins |
|---|---|---|
| Propylene | 4.1 | — |
| Butenes | 18.8 | — |
| Isobutylene | 69.5 | — |
| Butene-1 | 77.7 | — |
| Butene-2 | −32.6 | — |

TABLE XIV-continued

| | Conversion Weight Percent | Yield % C₃—C₄ Olefins |
|---|---|---|
| Total NC₄ | 2.9 | — |
| Butadiene | 91.8 | — |
| Total C₃—C₄ Olefins | 18.7 | — |
| C₆ + Oligomer | — | 17.9 |

From the above it can be seen that only 2.9 percent of the normal butenes were polymerized and butene-2 formation was equal to 32.6 percent of the original amount. The butene-2 formation accounts for 88.5 percent of the total butene-1 conversion by means of isomerization. The butene-2 concentration in the normal butene product was 92.6 percent by weight and very closely approaches the equilibrium value of 95.5. Additionally, 69.5 percent of the isobutylene was selectively polymerized to form a C₆+ gasoline boiling range oligomer product.

Oligomer product obtained in Run 4 has an API gravity of 58.2, a clear research number of 101.7, a clear motor research octane number of 84.7, and an oligomer fraction distribution as shown below in Table XV.

TABLE XV

| | Weight Percent |
|---|---|
| Dimer | 66.7 |
| Trimer | 28.9 |
| Tetramer | 3.8 |
| Pentamer | 0.7 |
| Hexamer | 0.0 |

The oligomer product was distilled using the distillation procedure of Example 1 with the results shown below in Table XVI.

TABLE XVI

| | |
|---|---|
| OP, °F. | 186° F.(58° C.) |
| EP, °F. | 470° F.(243° C.) |
| Percent Condensed at 760 MM | |
| 5 | 217° F.(103° C.) |
| 10 | 220° F.(104° C.) |
| 20 | 223° F.(106° C.) |
| 30 | 227° F.(108° C.) |
| 40 | 237° F.(114° C.) |
| 50 | 247° F.(119° C.) |
| 60 | 259° F.(126° C.) |
| 70 | 285° F.(141° C.) |
| 80 | 333° F.(167° C.) |
| 90 | 378° F.(192° C.) |
| 95 | 441° F.(227° C.) |
| Recovery % | 96.5 |
| Residue Percent | 1.5 |
| Loss Percent | 2.0 |

EXAMPLE 4

In this example an isothermal continuous polymerization run (Run 5) was made employing the novel polymerization catalyst to selectively polymerize isobutylene while simultaneously isomerizing butene-1 to butene-2 contained in a wet C₃-C₄ hydrocarbon feed mixture. The catalyst employed in the polymerization run was the hydrogen form of the synthetic mica montmorillonite containing 13.8 weight percent nickel (substantially all of the nickel being in the substituted form) and 3.6 weight percent fluorine. The hydrogen form was obtained by calcining the catalyst at 1000° F. (538° C.) overnight in air in a muffle furnace prior to charging to the reactor. The catalyst was in the form of 1/16 inch extrudates and had been prepared by the nickel fluoride preparation procedure described in application Ser. No. 291,263. The catalyst composition had been calcined and sulfided according to the procedures described in Example 2.

The hydrocarbon feed to the polymerization zone had the following composition:

TABLE XVII

| | Weight Percent |
|---|---|
| Ethane | 0.1 |
| Propylene | 29.0 |
| Propane | 9.4 |
| Isobutane | 22.3 |
| Butene-1 | 7.5 |
| Isobutylene | 7.5 |
| N-Butane | 7.5 |
| Trans-2-Butene | 9.4 |
| Cis-2-Butene | 6.4 |
| Isopentane | 0.5 |
| Butadiene | 0.3 |

The hydrocarbon feed was an aliquot blend of a butane-butene stream made in riser catalytic cracking and a pure propane-propylene stream normally charged to a cumene unit. The blend contained 64.4 percent by weight of the butane-butene stream which had been water washed prior to blending to lower combined nitrogen content to 0.2 ppm. The blended feed contained less than 0.2 ppm combined nitrogen, 16 ppm sulfur, and an equilibrium amount of dissolved water.

The polymerization process conditions employed in the run with the above defined catalyst and feed compositions are shown below in Table XVIII.

TABLE XVIII

| | Run 5 |
|---|---|
| Temp., °F. | 264.6(129° C.) |
| Pressure, psi | 600(42.3 kgs/cm²) |
| Space Velocity (liquid wt. hourly) | 1.0 |
| Catalyst, grams | 306.8 |
| Catalyst age, days | 40.1 |

Analysis of the product obtained in polymerization Run 5 shows the following conversions of the olefins in the feed mixture and yield of C₆+ oligomer:

TABLE XIX

| | Conversion Weight Percent | Yield % Wt. C₃—C₄ Olefins |
|---|---|---|
| Propylene | 8.4 | — |
| Butenes | 20.1 | — |
| Isobutylene | 73.5 | — |
| Butene-1 | 75.4 | — |
| Butene-2 | −31.8 | — |
| Total NC₄ | 2.8 | — |
| Butadiene | 100.0 | — |
| Total C₃—C₄ Olefins | 14.8 | — |
| C₆ + Oligomer | — | 11.8 |

From the above it can be seen that only 2.8 percent of the normal butenes were polymerized and butene-2 formation equalled 31.8 percent of the original amount. The butene-2 formation accounts for 91.1 percent of the total butene-1 conversion by means of isomerization. The butene-2 concentration in the normal butene product is 91.8 percent by weight and approaches the equilibrium value of 94.4. Additionally, 8.4 percent of the propylene and 73.5 percent of the isobutylene fractions contained in the feed mixture formed a C₆+ oligomer product.

The oligomer product contained in Run 5 had an API gravity of 59.0, a clear research octane number of 99.4 and an oligomer fraction distribution as shown below in Table XX:

TABLE XX

|  | Weight Percent |
| --- | --- |
| Dimer | 49.8 |
| Trimer | 41.6 |
| Tetramer | 6.6 |
| Pentamer | 1.4 |
| Hexamer | 0.6 |

The oligomer product was distilled using the distillation procedure of Example 1 with the results shown below in Table XXI:

TABLE XXI

| OP, °F. | 163° F.(73° C.) |
| --- | --- |
| EP, °F. | 509° F.(265° C.) |
| Percent Condensed at 760 MM | |
| 5 | 217° F.(103° C.) |
| 10 | 229° F.(109° C.) |
| 20 | 245° F.(118° C.) |
| 30 | 259° F.(126° C.) |
| 40 | 275° F.(135° C.) |
| 50 | 296° F.(147° C.) |
| 60 | 324° F.(162° C.) |
| 70 | 343° F.(173° C.) |
| 80 | 359° F.(193° C.) |
| 90 | 395° F.(202° C.) |
| 95 | 468° F.(242° C.) |
| Recovery Percent | 97.9 |
| Residue Percent | 1.4 |
| Loss Percent | 0.7 |

EXAMPLE 5

In this example a continuous polymerization run (Run 6) was made employing the novel polymerization catalyst to selectively polymerize isobutylene contained in a substantially sulfur-free $C_4$ hydrocarbon feed mixture. The catalyst employed in the polymerization run was the hydrogen form of the synthetic mica montmorillonite containing 9.7 weight percent nickel (substantially all of the nickel being in the substituted form) and 0.82 weight percent fluorine. During synthesis of the catalyst nickel was incorporated by means of nickel acetate. The catalyst composition had been calcined at a temperature of 956° F. (513° C.), a pressure of 25 psig (1.8 kgs/cm$^2$), and at a space velocity of 318 gas volumes per hour of dry air for two hours. Following calcination, the catalyst composition was cooled in nitrogen to the polymerization run temperature.

The hydrocarbon feed to the polymerization zone comprised a blend of chemically pure grade hydrocarbons and had the following composition:

TABLE XXII

|  | Weight Percent |
| --- | --- |
| Isobutane | 51.1 |
| Butene-1 | 9.9 |
| Isobutylene | 10.6 |
| N-Butane | 1.8 |
| Cis-2-Butene | 26.6 |

The feed was dried over 3 angstrom molecular sieves prior to introduction into the polymerization reactor.

The polymerization process conditions employed in the run with the above defined catalyst and feed compositions are shown below in Table XXIII:

TABLE XXIII

|  | Run 6 |
| --- | --- |
| Average Temp., °F. | 132(56° C.) |

TABLE XXIII-continued

|  | Run 6 |
| --- | --- |
| Pressure, psi | 400(28.3 kgs/cm$^2$) |
| Space Velocity (liquid weight hourly) | 2.0 |
| Catalyst, Grams | 64.0 |
| Catalyst Age, Days | 5.3 |

Analysis of the product obtained in polymerization Run 6 shows the following conversions of the olefins in the feed mixture and yield of $C_6+$ oligomer:

TABLE XXIV

|  | Conversion Percent | Yield % Wt. $C_4$ Olefins |
| --- | --- | --- |
| Butenes | 24.6 | — |
| Isobutylene | 79.2 | — |
| Butene-1 | 16.0 | — |
| Butenes-2 | 6.0 | — |
| Total NC$_4$ | 8.7 | — |
| Total $C_4$ Olefins | 24.6 | — |
| $C_6$ + Oligomer | — | 22.2 |

From the above it can be seen that isobutylene was selectively polymerized at a substantially lower temperature and higher space velocity than was possible when employing the sulfided form of the catalyst composition with sulfur in the feed. Undesirably, the extent of n-butene polymerization was somewhat higher and the extent of butene-1 isomerization to butene-2 was much less than that obtained when employing the sulfided form of the catalyst with some sulfur in the feed. Additionally, several days of operation were necessary before the activity of the catalyst was moderated to the extent that n-butene polymerization fell below 10 percent and the amount of tetramer and heavier material in the oligomer product fell below 12 weight percent.

The oligomer product had an API gravity of 55.4, a clear research octane number of 100.8, and an oligomer fraction distribution as shown below in Table XXV:

TABLE XXV

|  | Weight Percent |
| --- | --- |
| Dimer | 65.2 |
| Trimer | 31.7 |
| Tetramer | 3.1 |
| Pentamer | 0.0 |
| Hexamer | 0.0 |

EXAMPLE 6

In previous examples the selective polymerization of isobutylene in a $C_4$ olefins feed mixture has been demonstrated. In this example there is demonstrated a polymerization process whereby the novel polymerization catalyst can be employed to polymerize from 85 to 100 percent of the isobutylene and from 12 to 35 percent of the normal butenes and propylene contained in a $C_3$-$C_4$ olefin feed mixture by varying the process conditions. Therefore, this example demonstrates the effectiveness of the inventive process to form $C_3$-$C_4$ oligomer products.

The catalyst composition of Example 4 was employed in a continuous polymerization run (Run 7) utilizing a $C_3$-$C_4$ feed mixture having the same composition as the feed mixture of Example 4.

The polymerization process conditions employed in the run are shown below in Table XXVI:

TABLE XXVI

| | Run 7 |
|---|---|
| Temp., °F. | 280 (138° C.) |
| Pressure, psi | 900(63.4 kgs/cm²) |
| Space Velocity | |
| (liquid wt. hourly) | 1.0 |
| Catalyst, grams | 306.8 |
| Catalyst age, days | 44.0 |

Analysis of the product obtained in polymerization Run 7 shows the following conversions of the olefins in the feed mixture and yield of $C_6+$ oligomer:

TABLE XXVII

| | Conversion Percent | Yield % Wt. $C_3-C_4$ Olefins |
|---|---|---|
| Propylene | 24.2 | — |
| Butenes | 34.0 | — |
| Isobutylene | 90.3 | — |
| Butene-1 | 81.0 | — |
| Butene-2 | −15.4 | — |
| Total $NC_4$ | 15.8 | — |
| Butadiene | 100.0 | — |
| Total $C_3-C_4$ Olefins | 29.5 | — |
| $C_6$ + Oligomer | — | 26.4 |

About 48.7 percent of the butene-1 contained in the feed mixture was isomerized to butene-2 and about 32.4 percent of the butene-1 was polymerized to form a portion of the oligomer product. The n-butene product comprised 92.7 percent by weight butene-2 and closely approached the equilibrium value of 94.1.

The oligomer product contained in Run 7 had an API gravity of 57.3, a clear research octane number of 98.1 and an oligomer fraction distribution as shown below:

TABLE XXVIII

| | Weight Percent |
|---|---|
| Dimer | 64.3 |
| Trimer | 30.1 |
| Tetramer | 4.8 |
| Pentamer | 0.5 |
| Hexamer | 0.1 |

The oligomer product was distilled using the distillation procedure of Example 1 with the results shown below in Table XXIX:

TABLE XXIX

| | |
|---|---|
| OP, °F. | 114° F.(46° C.) |
| EP, °F. | 470° F.(243° C.) |
| Percent Condensed at 760 MM | |
| 5 | 199° F.(93° C.) |
| 10 | 216° F.(102° C.) |
| 20 | 231° F.(111° C.) |
| 30 | 244° F.(118° C.) |
| 40 | 256° F.(124° C.) |
| 50 | 274° F.(134° C.) |
| 60 | 303° F.(151° C.) |
| 70 | 335° F.(168° C.) |
| 80 | 355° F.(179° C.) |
| 90 | 400° F.(204° C.) |
| 95 | 470° F.(243° C.) |
| Recovery Percent | 96.0 |
| Residue Percent | 2.3 |
| Loss Percent | 1.7 |

Although the invention has been described with reference to specific embodiments, references, and details, various modifications and changes will be apparent to one skilled in the art and are contemplated to be embraced in this invention.

We claim:

1. A process which comprises contacting a $C_2-C_4$ mono-olefin feed with a catalyst under polymerization conditions to include a temperature in the range of 250°–480° F., a pressure in the range of 400–1500 psig, and a space velocity in the range of 0.5 to 4.0 liquid weight hourly, said catalyst comprising:

a dried and calcined laminar 2:1 layer-lattice aluminosilicate mineral possessing layer-lattice unit cells, each cell having an inherent negative charge balanced by cations exterior to said unit cell, said mineral corresponding to the following overall formula prior to drying and calcining:

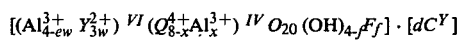

Where Y is selected from the class consisting of nickel, cobalt and mixtures thereof;

Q is at least 0.95 mol fraction silicon ions, the remainder consisting of tetravalent ions having an ionic radius not to exceed 0.65 Å;

C is at least one charge-balancing cation; and where e has a numerical value from 2 to 3 inclusive;

w has a numerical value from 0.01 to 2 inclusive, with the proviso that the quantity ew have a numerical value from 0.02 to 4 inclusive;

f has a value of 4 or less;

x has a numerical value from 0.05 to 2.0 inclusive;

y is the valence of the cation C;

d is the number of cations C where the product $dy = x + 3(e-2)w$;

and recovering therefrom a low pour oligomer product having more than 75% by weight of the oligomer boiling above 200° F.

2. The process of claim 1 wherein said catalyst is in the sulfided form.

3. The catalyst of claim 2 wherein said mono-olefin feed comprises a mixture of $C_3$ and $C_4$ mono-olefins.

4. The process of claim 1 wherein said catalyst also contains a hydrogenation component selected from the group consisting of Group VI and Group VIII deposited thereon.

5. The process of claim 4 wherein said hydrogenation component is selected from the group consisting of nickel and cobalt and wherein the concentration of said hydrogenation component is in the range of 0.01 to 5 weight percent of said catalyst.

6. A process which comprises contacting a $C_2-C_5$ olefin feed containing at least one tertiary alpha olefin with a catalyst under polymerization conditions to include a temperature in the range of 120° to 380° F., a pressure in the range of 400 to 1500 psig, and a space velocity in the range of 0.5 to 4.0 liquid weight hourly, said catalyst comprising:

a dried and calcined laminar 2:1 layer-lattice aluminosilicate mineral possessing layer-lattice unit cells, each cell having an inherent negative charge balanced by cations exterior to said unit cell, said mineral corresponding to the following overall formula prior to drying and calcining:

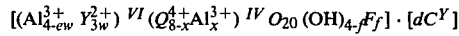

Where Y is selected from the class consisting of nickel, cobalt and mixtures thereof;

Q is at least 0.95 mol fraction silicon ions, the remainder consisting of tetravalent ions having an ionic radius not to exceed 0.65 Å;

C is at least one charge-balancing cation; and where e has a numerical value from 2 to 3 inclusive;

w has a numerical value from 0.01 to 2 inclusive, with the proviso that the quantity ew have a numerical value from 0.02 to 4 inclusive;

f has a value of 4 or less;

x has a numerical value from 0.05 to 2.0 inclusive;

y is the valence of the cation C;

d is the number of cations C where the product $dy = x + 3(e-2)w$;

and recovering therefrom a gasoline boiling oligomer containing at least 50 weight percent of said tertiary alpha olefin.

7. The process of claim 6 wherein at least 75%, on a weight basis, of the butene-1 contained in said olefin feed is isomerized to butene-2.

8. The process of claim 7 wherein said tertiary alpha olefin is isobutylene and wherein oligomerization of said isobutylene will be at least 50 weight percent.

9. The process of claim 6 wherein said catalyst is in the sulfided form.

10. The process of claim 9 wherein said tertiary alpha olefin is selected from the group consisting of isobutylene and 2-methyl-butene-1.

11. A process which comprises contacting a $C_4$ hydrocarbon mixture containing butene-1 and isobutylene with a catalyst under polymerization conditions to include a temperature in the range of 120° to 380° F., a pressure in the range of 400 to 1500 psig, and a space velocity in the range of 0.5 to 4.0 liquid weight hourly, said catalyst being in the sulfided form and comprising:

a dried and calcined laminar 2:1 layer-lattice aluminosilicate mineral possessing layer-lattice unit cells, each cell having an inherent negative charge balanced by cations exterior to said unit cell, said mineral corresponding to the following overall formula prior to drying and calcining:

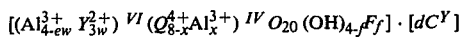

Where Y is selected from the class consisting of nickel, cobalt and mixtures thereof;

Q is at least 0.95 mol fraction silicon ions, the remainder consisting of tetravalent ions having an ionic radius not to exceed 0.65 Å;

C is at least one charge-balancing cation; and where e has a numerical value from 2 to 3 inclusive;

w has a numerical value from 0.01 to 2 inclusive, with the proviso that the quantity ew have a numerical value from 0.02 to 4 inclusive;

f has a value of 4 or less;

x has a numerical value from 0.05 to 2.0 inclusive;

y is the valence of the cation C;

d is the number of cations C where the product $dy = x + 3(e-2)w$;

and recovering therefrom a gasoline boiling range oligomer having a clear research octane number of 100.5 to 103, isobutylene oligomerization being from 50 to 80% by weight, and at least 75% of the butene-1 being isomerized to butene-2.

12. A process which comprises contacting a hydrocarbon feed containing propylene and isobutylene with a catalyst under polymerization conditions to include a temperature in the range of 120° to 380° F., a pressure in the range of 400 to 1500 psig, and a space velocity in the range of 0.5 to 4.0 liquid weight hourly, said catalyst comprising:

a dried and calcined laminar 2:1 layer-lattice aluminosilicate mineral possessing layer-lattice unit cells, each cell having an inherent negative charge balanced by cations exterior to said unit cell, said mineral corresponding to the following overall formula prior to drying and calcining:

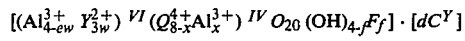

Where Y is selected from the class consisting of nickel, cobalt and mixtures thereof;

Q is at least 0.95 mol fraction silicon ions, the remainder consisting of tetravalent ions having an ionic radius not to exceed 0.65 Å;

C is at least one charge-balancing cation; and where e has a numerical value from 2 to 3 inclusive;

w has a numerical value from 0.01 to 2 inclusive, with the proviso that the quantity ew have a numerical value from 0.02 to 4 inclusive;

f has a value of 4 or less;

x has a numerical value from 0.05 to 2.0 inclusive;

y is the valence of the cation C;

d is the number of cations C where the product $dy = x + 3(e-2)w$;

and recovering therefrom a gasoline boiling oligomer containing from 85 to 98 weight percent of said isobutylene and from 12 to 40 weight percent of said propylene contained in said feed, the liquid oligomer product having a clear research octane number in the range of 98-100.

* * * * *